United States Patent [19]
Willard

[11] Patent Number: 5,971,967
[45] Date of Patent: Oct. 26, 1999

[54] URETHRAL DEVICE WITH ANCHORING SYSTEM

[75] Inventor: Lloyd K. Willard, Miltona, Minn.

[73] Assignee: AbbeyMoor Medical, Inc., Miltona, Minn.

[21] Appl. No.: 08/914,487

[22] Filed: Aug. 19, 1997

[51] Int. Cl.$^6$ ..................................................... A61M 5/00
[52] U.S. Cl. ..................... 604/264; 604/175; 604/500; 600/29; 600/30
[58] Field of Search ..................................... 604/175, 174, 604/500, 508, 264, 523, 93; 600/29, 30

[56] References Cited

U.S. PATENT DOCUMENTS

| | | |
|---|---|---|
| 207,932 | 9/1878 | Alvord . |
| 547,047 | 10/1895 | Thornton et al. . |
| 707,775 | 8/1902 | Harris . |
| 1,045,326 | 11/1912 | Ruflin . |
| 1,589,056 | 6/1926 | Drummond . |

(List continued on next page.)

FOREIGN PATENT DOCUMENTS

| | | |
|---|---|---|
| 0 753 289 A1 | 1/1997 | European Pat. Off. . |
| 564.832 | 1/1924 | France . |
| 2 219 941 | 12/1989 | United Kingdom . |
| 2 219 943 | 12/1989 | United Kingdom . |
| WO 95/17862 | 7/1995 | WIPO . |
| WO 97/06758 | 2/1997 | WIPO . |
| WO 97/25090 | 7/1997 | WIPO . |
| WO 98/06354 | 2/1998 | WIPO . |

OTHER PUBLICATIONS

Hayes, O., M.D., "Spiral Urethral Dilator," *Jour. A. M. A.*, Sep. 18, 1926, vol. 87, No. 12, pp. 939–940.

*Primary Examiner*—John D. Yasko
*Attorney, Agent, or Firm*—Brinks Hofer Gilson & Lione

[57] ABSTRACT

A device that comprises a tubular-shaped body that is insertable into a body passageway or cavity, in particular the urethra, and that has an exterior surface having one or more anchors located thereon that aid in movement of the device with a minimum of trauma during placement and that aid in securing the device within the passageway or cavity during use. The device may be inserted into either the urethra, bladder neck, or bladder. The anchors can vary in height, length, number, compressiveness, axial placement, material characteristics, and helix angle. According to a further aspect, the one or more anchors are in the form of partial spiral helixes that function to move and secure the device within the human urethra. The partial spiral helixes have structures that allow for the longitudinal movement of the device during positioning procedures.

93 Claims, 10 Drawing Sheets

U.S. PATENT DOCUMENTS

| | | |
|---|---|---|
| 1,644,919 | 10/1927 | Hayes . |
| 1,688,795 | 10/1928 | Aas . |
| 1,714,741 | 5/1929 | Urquhart . |
| 2,078,686 | 4/1937 | Rowe . |
| 2,450,217 | 9/1948 | Alcorn . |
| 3,136,316 | 6/1964 | Beall . |
| 3,331,371 | 7/1967 | Rocchi et al. . |
| 3,419,008 | 12/1968 | Plishner . |
| 3,428,046 | 2/1969 | Remer et al. . |
| 3,498,286 | 3/1970 | Polanyi et al. . |
| 3,503,400 | 3/1970 | Osthagen et al. . |
| 3,630,206 | 12/1971 | Gingold . |
| 3,642,004 | 2/1972 | Osthagen et al. . |
| 3,731,670 | 5/1973 | Loe . |
| 3,742,958 | 7/1973 | Rundles . |
| 3,768,102 | 10/1973 | Kwan-Gett et al. . |
| 3,788,327 | 1/1974 | Donowitz et al. . |
| 3,797,478 | 3/1974 | Walsh et al. . |
| 3,799,172 | 3/1974 | Szpur . |
| 3,812,841 | 5/1974 | Isaacson . |
| 3,815,608 | 6/1974 | Spinosa et al. . |
| 3,831,588 | 8/1974 | Rindner . |
| 3,863,622 | 2/1975 | Buuck . |
| 3,876,234 | 4/1975 | Harms . |
| 3,902,501 | 9/1975 | Citron et al. . |
| 3,924,631 | 12/1975 | Mancusi, Jr. . |
| 3,939,821 | 2/1976 | Roth . |
| 3,946,724 | 3/1976 | La Balme . |
| 4,024,855 | 5/1977 | Bucalo . |
| 4,249,536 | 2/1981 | Vega . |
| 4,266,815 | 5/1981 | Cross . |
| 4,269,192 | 5/1981 | Matsuo . |
| 4,344,435 | 8/1982 | Aubin . |
| 4,350,161 | 9/1982 | Davis, Jr. . |
| 4,432,757 | 2/1984 | Davis, Jr. . |
| 4,501,580 | 2/1985 | Glassman . |
| 4,553,533 | 11/1985 | Leighton . |
| 4,579,554 | 4/1986 | Glassman . |
| 4,670,008 | 6/1987 | Von Albertini . |
| 4,679,546 | 7/1987 | van Wallwijk et al. . |
| 4,711,249 | 12/1987 | Brooks . |
| 4,760,847 | 8/1988 | Vaillancourt . |
| 4,795,439 | 1/1989 | Guest . |
| 4,801,293 | 1/1989 | Jackson . |
| 4,809,709 | 3/1989 | Brooks . |
| 4,815,472 | 3/1989 | Wise et al. . |
| 4,820,288 | 4/1989 | Isono . |
| 4,822,333 | 4/1989 | Lavarenne . |
| 4,909,785 | 3/1990 | Burton et al. . |
| 4,919,653 | 4/1990 | Martinez et al. . |
| 4,934,999 | 6/1990 | Bader . |
| 4,946,449 | 8/1990 | Davis, Jr. . |
| 4,955,858 | 9/1990 | Drews . |
| 4,969,896 | 11/1990 | Shors . |
| 5,004,454 | 4/1991 | Beyar et al. . |
| 5,018,529 | 5/1991 | Tenerz et al. . |
| 5,030,199 | 7/1991 | Barwick et al. . |
| 5,030,227 | 7/1991 | Rosenbluth et al. . |
| 5,041,092 | 8/1991 | Barwick . |
| 5,087,252 | 2/1992 | Denard . |
| 5,088,980 | 2/1992 | Leighton . |
| 5,129,910 | 7/1992 | Phan et al. . |
| 5,140,999 | 8/1992 | Ardito . |
| 5,239,982 | 8/1993 | Trauthen . |
| 5,246,445 | 9/1993 | Yachia et al. . |
| 5,271,735 | 12/1993 | Greenfeld et al. . |
| 5,275,169 | 1/1994 | Afromowitz et al. . |
| 5,279,567 | 1/1994 | Ciaglia et al. . |
| 5,312,430 | 5/1994 | Rosenbluth et al. . |
| 5,334,185 | 8/1994 | Giesy et al. . |
| 5,366,506 | 11/1994 | Davis . |
| 5,380,268 | 1/1995 | Wheeler . |
| 5,383,866 | 1/1995 | Chang . |
| 5,389,077 | 2/1995 | Melinyshyn et al. . |
| 5,423,809 | 6/1995 | Klicek . |
| 5,425,382 | 6/1995 | Golden et al. . |
| 5,427,114 | 6/1995 | Colliver et al. . |
| 5,437,290 | 8/1995 | Bolger et al. . |
| 5,437,604 | 8/1995 | Kulisz et al. . |
| 5,445,144 | 8/1995 | Wodicka et al. . |
| 5,470,350 | 11/1995 | Buchholtz et al. . |
| 5,472,405 | 12/1995 | Buchholtz et al. . |
| 5,483,832 | 1/1996 | Pauser et al. . |
| 5,486,191 | 1/1996 | Pasricha et al. . |
| 5,492,131 | 2/1996 | Galel . |
| 5,507,731 | 4/1996 | Hernandez et al. . |
| 5,509,888 | 4/1996 | Miller . |
| 5,512,032 | 4/1996 | Kulisz et al. . |
| 5,514,178 | 5/1996 | Torchio . |
| 5,520,650 | 5/1996 | Zadini et al. . |
| 5,520,665 | 5/1996 | Fleetwood . |
| 5,527,336 | 6/1996 | Rosenbluth et al. . |
| 5,549,577 | 8/1996 | Siegel et al. . |
| 5,558,091 | 9/1996 | Acker et al. . |
| 5,601,537 | 2/1997 | Frassica . |
| 5,618,257 | 4/1997 | Kulisz et al. . |
| 5,701,916 | 12/1997 | Kulisz et al. . |
| 5,711,314 | 1/1998 | Ardito . |
| 5,713,877 | 2/1998 | Davis . |
| 5,718,686 | 2/1998 | Davis . |
| 5,722,932 | 3/1998 | Kulisz et al. . |

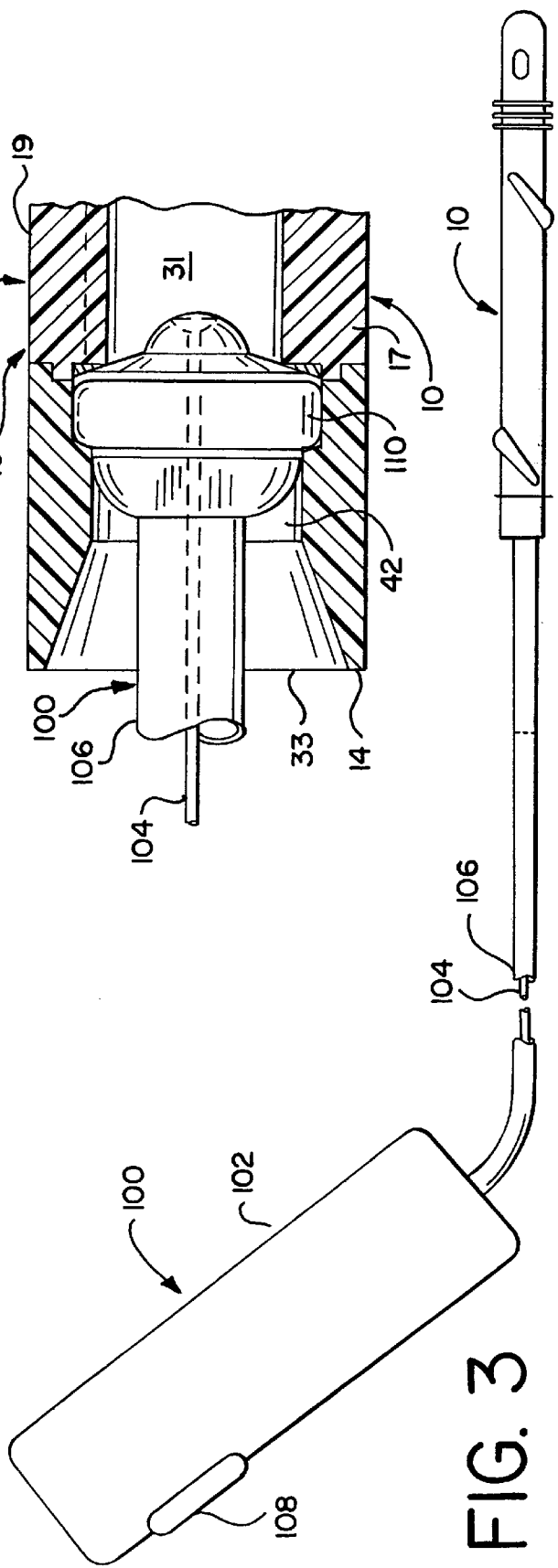

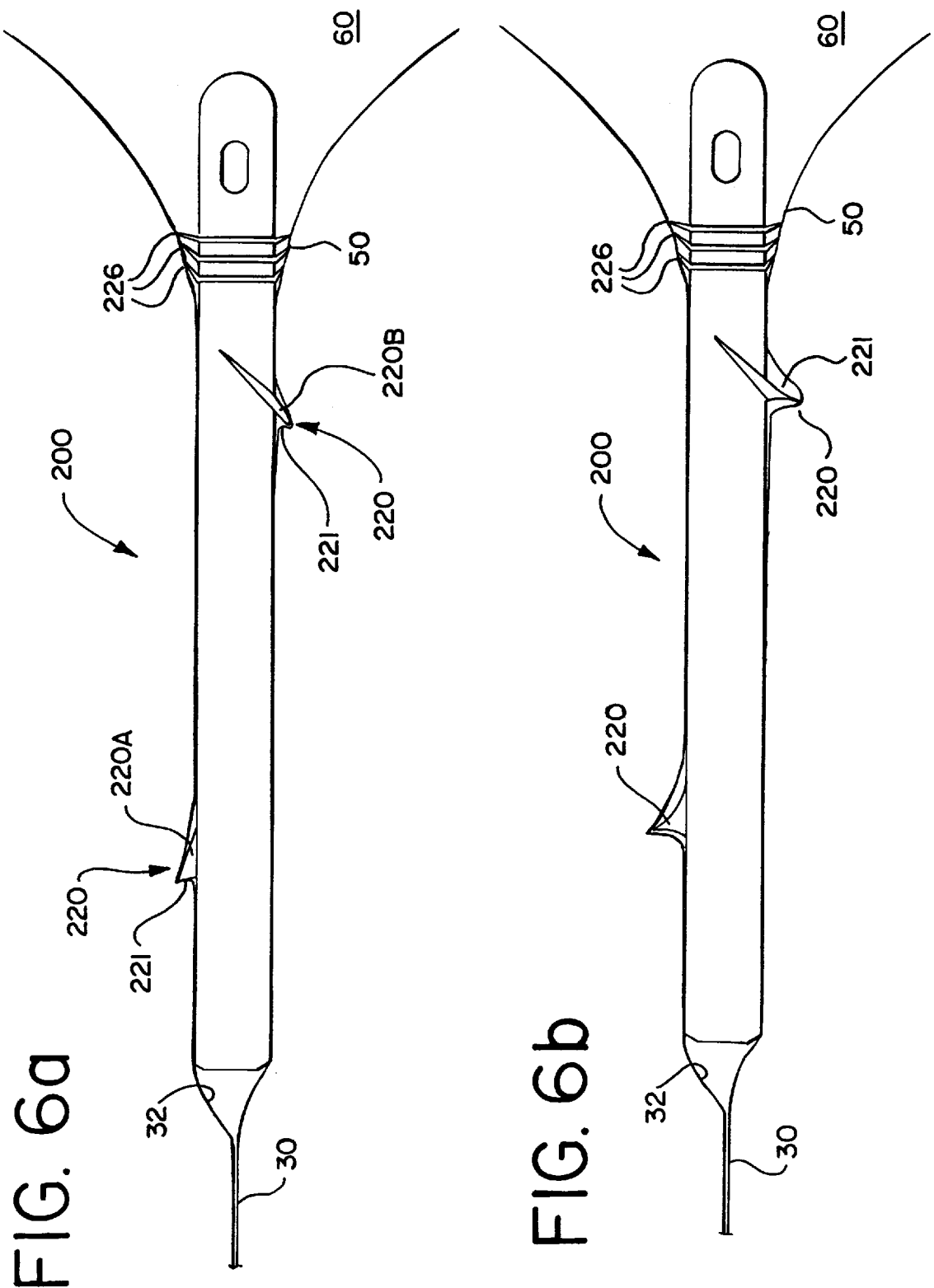

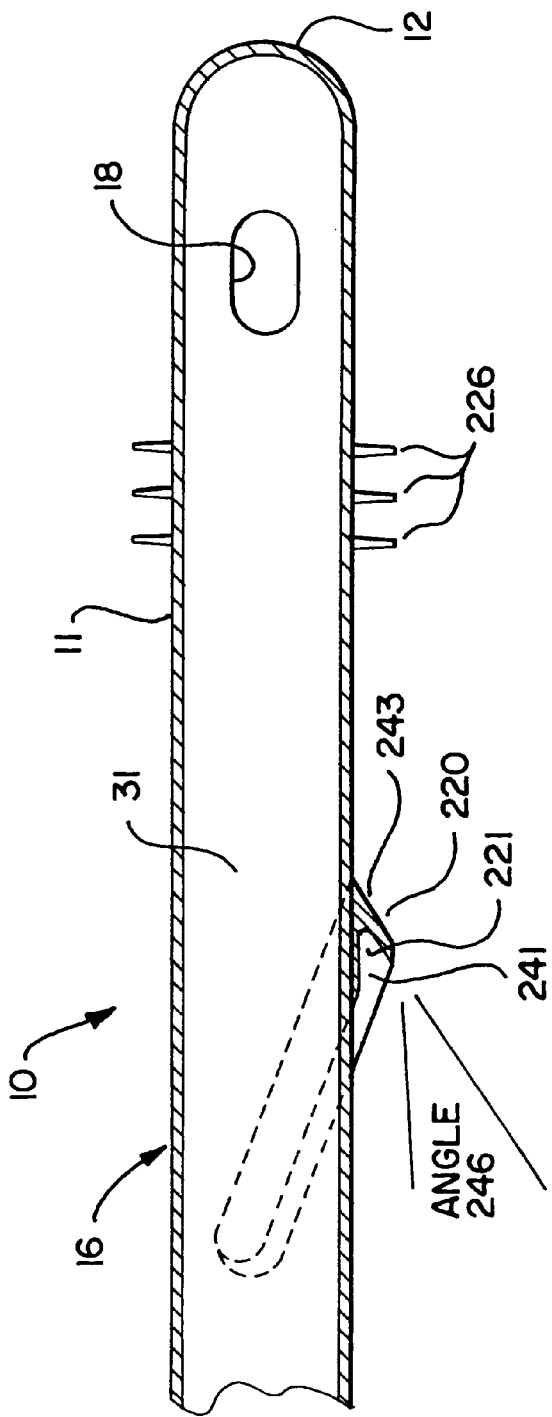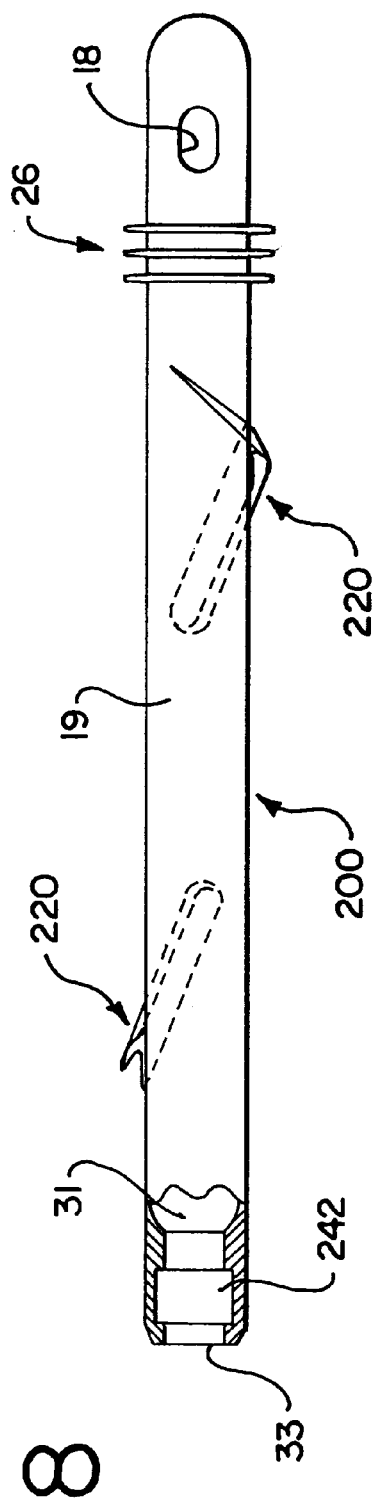

FIG. 14
FIG. 15
FIG. 16
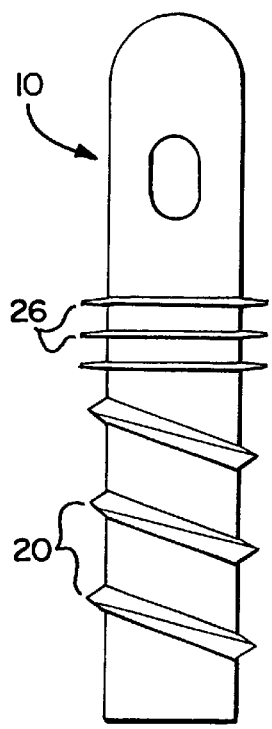
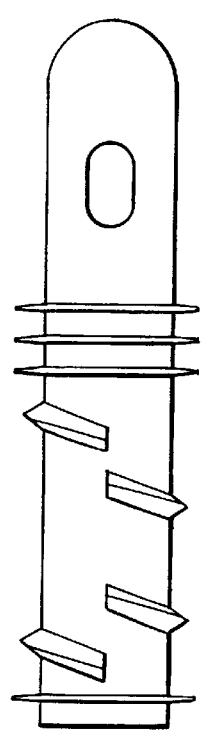
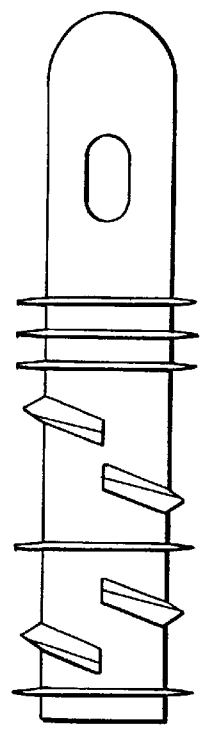
FIG. 17
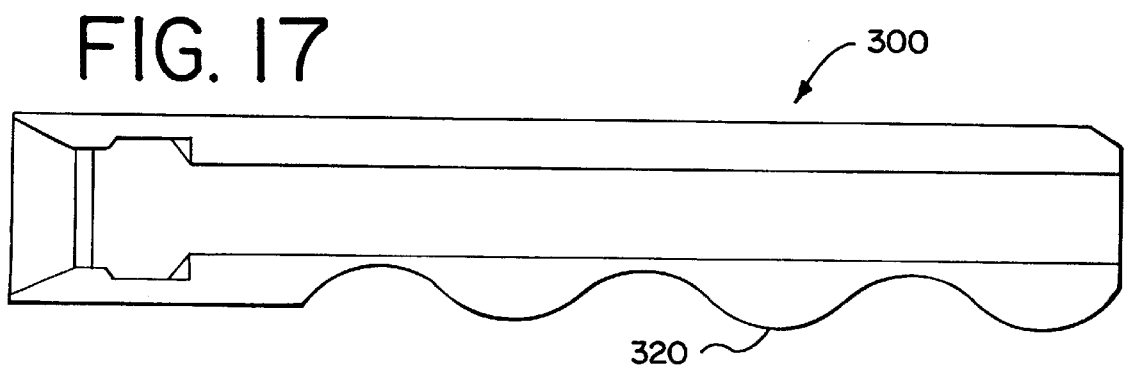
FIG. 18
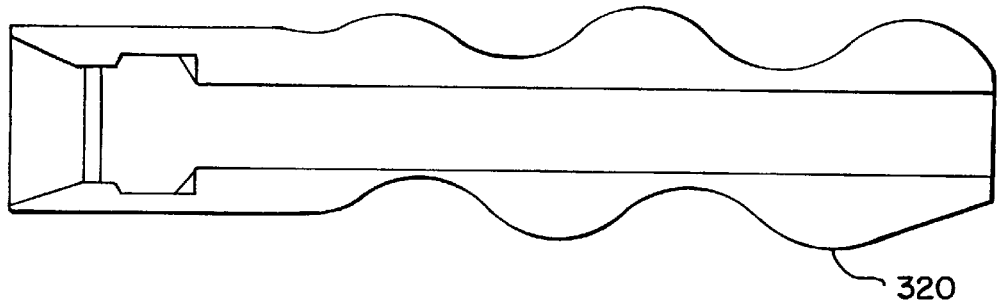

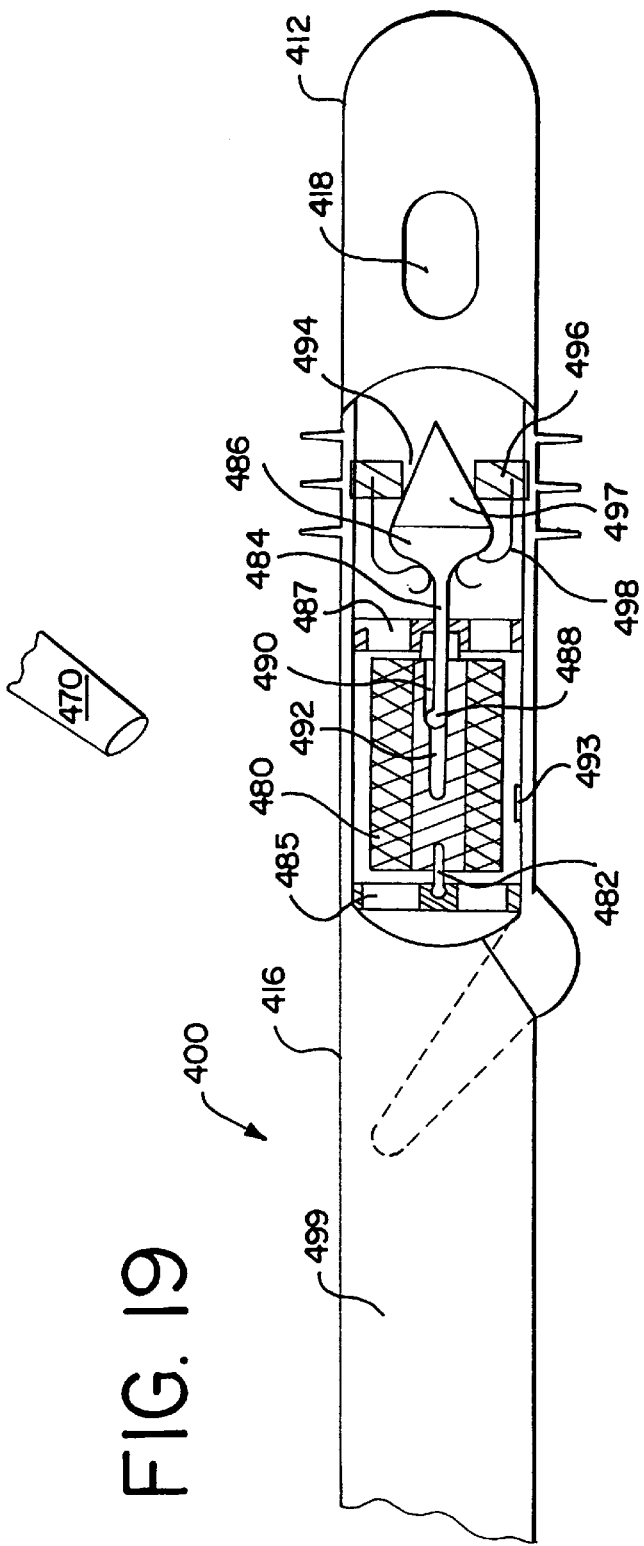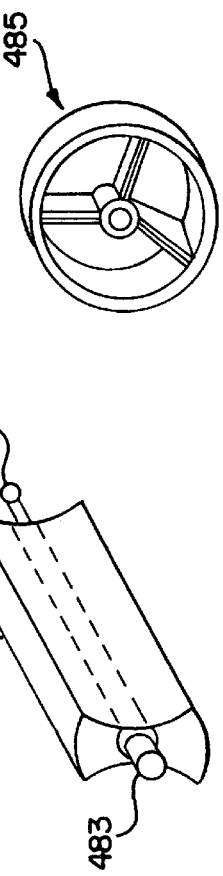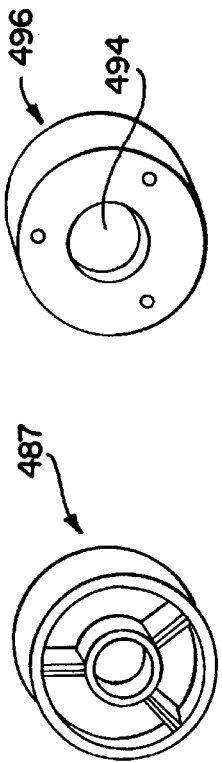

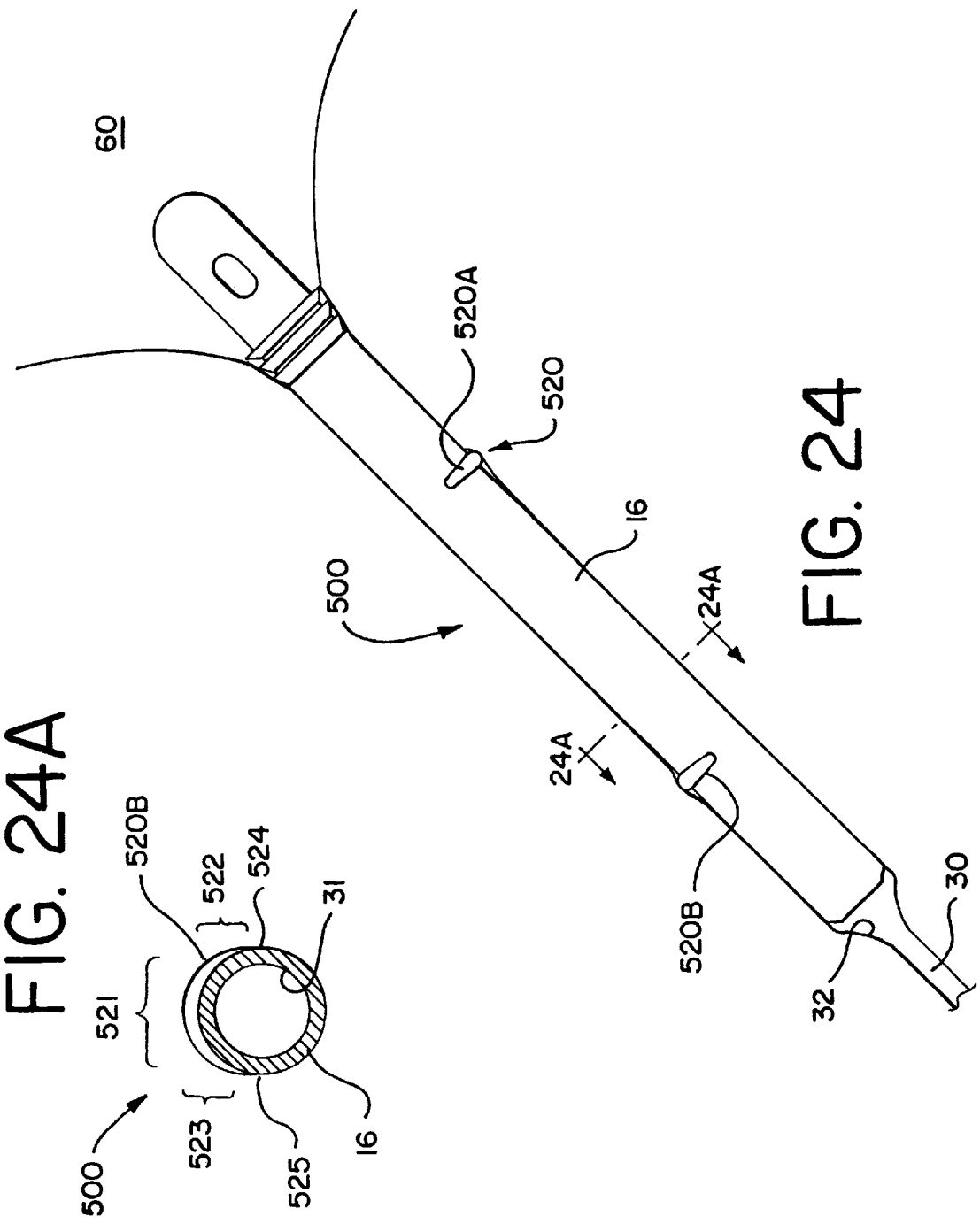

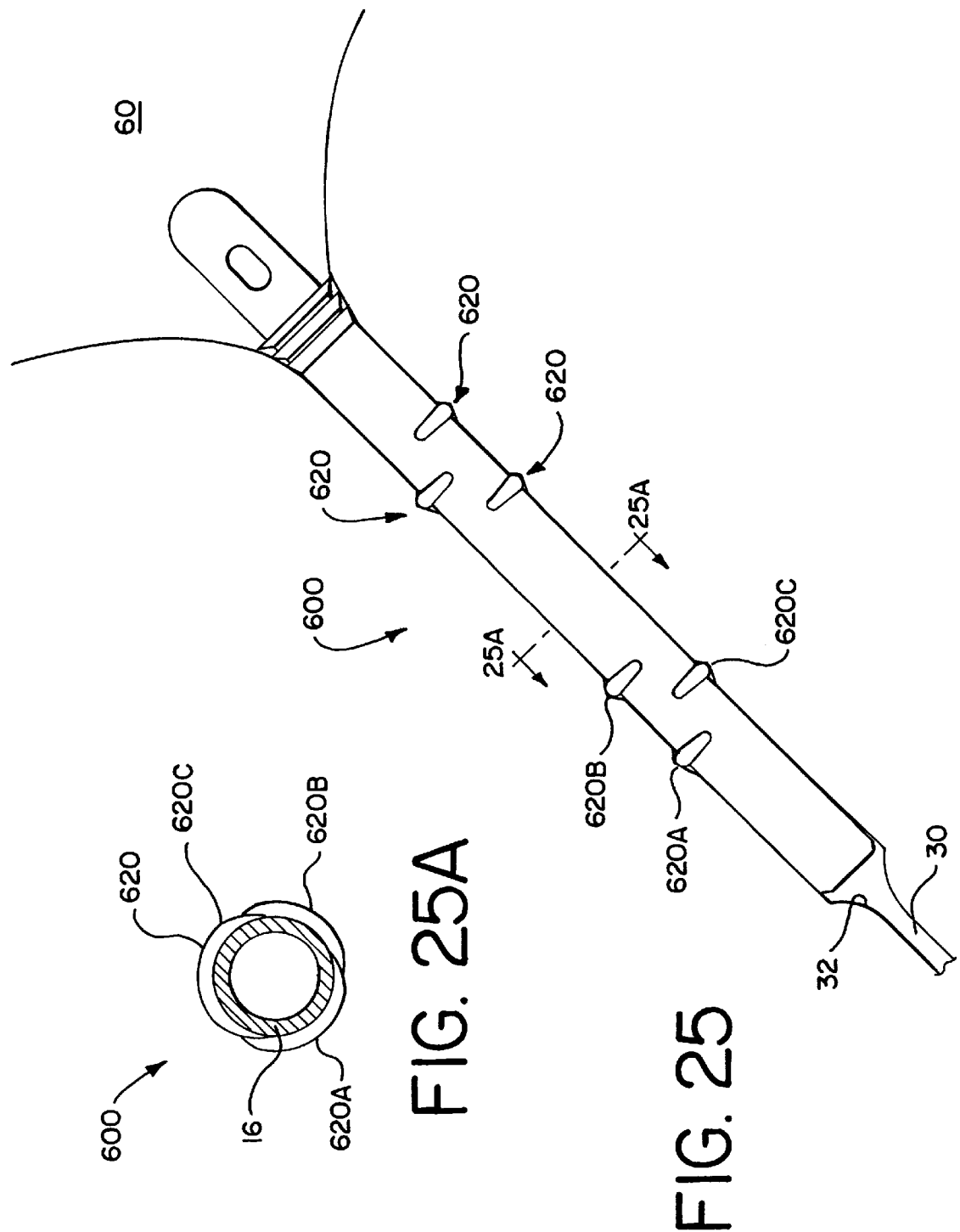

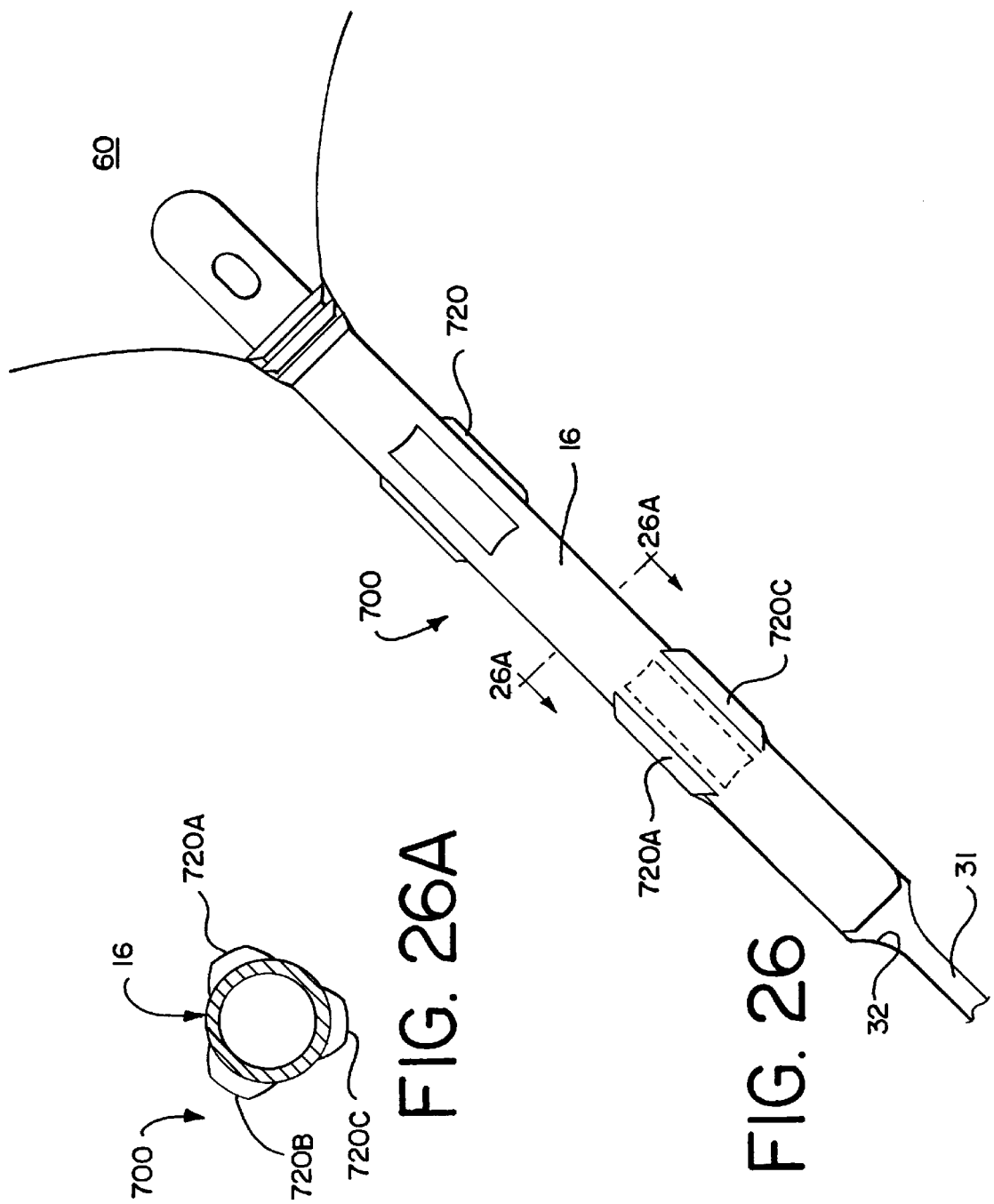

URETHRAL DEVICE WITH ANCHORING SYSTEM

BACKGROUND OF THE INVENTION

The present invention relates generally to urethral apparatuses and methods of use, and more particularly to a urethral apparatus that can be positioned in the urethra for short-term or long-term use, relatively comfortably but securely.

Urinary problems can have serious consequences, particularly when the problem is one of retention or ischuria. Urine flow problems include urine retention, incontinence, and difficult urination. Retention can result from any of a number of causes, including without limitation, spinal cord injury or tumors, coma, typhoid, peritonitis, prostatic enlargement, urethral stricture, urethritis, cystitis, bladder tumors, urethral calculus, Parkinson's disease, prostatitis, or multiple sclerosis. Patients suffering from these and other conditions often require some interventional means to periodically drain the bladder. Failure to do so can result in damage of the epithelium and detrusor muscles associated with the bladder, and an increased potential for bacterial invasion and urinary tract infection potentially leading to life-threatening kidney failure.

Another urine flow problem is that of incontinence, which is the inability to retain urine because of paralysis or relaxation of sphincters or contraction of longitudinal muscular layers of the bladder. Incontinence can also occur in coma, epileptic seizure, spinal cord injury or tumors associated with the spinal cord, spinal meningitis, or local irritation of the bladder. Incontinence is usually categorized as either stress incontinence, in which urine is expelled during stresses such as exercise, coughing, and laughing; urge incontinence, in which the patient in unable to control the urge to urinate in part due to uninhibited bladder contractions; or mixed incontinence, in which the patient experiences both stress and urge incontinence.

Difficult urination or dysuria can result from urethral strictures, enlarged prostates, atony and impairment of the bladder's muscular power, and inflammatory conditions involving the urethra, bladder, or lower ureter.

Devices have been developed to be positioned in the urethra and/or bladder to correct the problems of urine flow. Urinary drainage catheters and devices have a long history, and many approaches have been taken to keeping these devices in place. Many of these devices suffer from one or more problems. For example, some of these devices may have been difficult or uncomfortable to place into position or to retain in position after placement. Also, some of these devices may have tended to leak or become dislodged unintentionally. Further, some of these devices have led to infections.

Accordingly, it is an object to provide a device that is easily and atraumatically inserted and removed. It is another object to provide a device that can be positioned in the urethra with a minimum of stress to the urethra and with a minimum of bacterial migration. It is still a further object to provide a device that can remain in position in the urethra and withstand pressure impulses due to stresses such as coughing, laughing, or exercising.

SUMMARY OF THE INVENTION

To address the above concerns, the present invention provides a device that comprises a tubular-shaped body that in insertable into a body passageway or cavity, in particular the urethra, and that has an exterior surface having one or more anchors located thereon that aid in movement of the device with a minimum of trauma during placement and that aid in securing the device within the passageway or cavity during use. The device may be inserted into either the urethra, bladder neck, or bladder.

According to a further aspect, the one or more anchors on the device are in the form of partial spiral helixes that function to move and secure the device within the human urethra. The partial spiral helical anchors have structures that allow for the longitudinal movement of the device during positioning procedures. These anchors can vary in height, length, number, compressiveness, axial placement, material characteristics, and helix angle. In addition, leading and trailing edges associated with each of the anchors provide a tapered gradual increase up to a maximum height of each of the anchors to ease insertion and removal of the device and to prevent a shearing effect that could result from a blunt or aggressive leading edge.

BRIEF DESCRIPTION OF THE DRAWINGS

FIG. 3 is an elevational view of the urethral device of FIG. 1 coupled with an installation tool.

FIGS. 4 and 5 are partial sectional views illustrating the coupling apparatus at the interface of the installation tool and the urethral device shown in FIG. 3.

FIGS. 6a and 6b are expanded elevational views showing an alternate embodiment of the urethra device positioned within the urethra.

FIG. 7 is a sectional view of the distal portion of the embodiment of FIGS. 6a, and 6b.

FIG. 8 is a partial sectional elevational view of the embodiment of FIGS. 6a, 6b, and 7.

FIGS. 14–16 are elevational views of further alternate embodiments of the urethral device for human females.

FIGS. 17 and 18 are views of further alternate embodiments of the urethral device showing sinusoidal surfaces.

FIG. 19 is a partial elevational sectional assembly view of an embodiment of the urethral device with a magnetically-actuated valve assembly.

FIG. 20 is a perspective view of the magnetic tumbler in the embodiment of FIG. 19.

FIG. 21 is an expanded perspective view of the distal support flange of FIG. 19.

FIG. 22 is an expanded perspective view of the proximal support flange of FIG. 19.

FIG. 23 is an expanded perspective view of the seat of FIG. 19.

FIG. 24 is an elevational view of another embodiment of an indwelling urethral device positioned within the urethra.

FIG. 24A is a cross sectional view of the embodiment of FIG. 24 taken along line 24A–24A'.

FIG. 25 is an elevational view of a further embodiment of an indwelling urethral device positioned within the urethra.

FIG. 25A is a cross sectional view of the embodiment of FIG. 25 taken along line 25A–25A'.

FIG. 26 is an elevational view of still another embodiment of an indwelling urethral device positioned within the urethra.

FIG. 26A is a cross sectional view of the embodiment of FIG. 26 taken along line 26A–26A'.

DETAILED DESCRIPTION OF THE PRESENTLY PREFERRED EMBODIMENTS

Figures 1, 2:
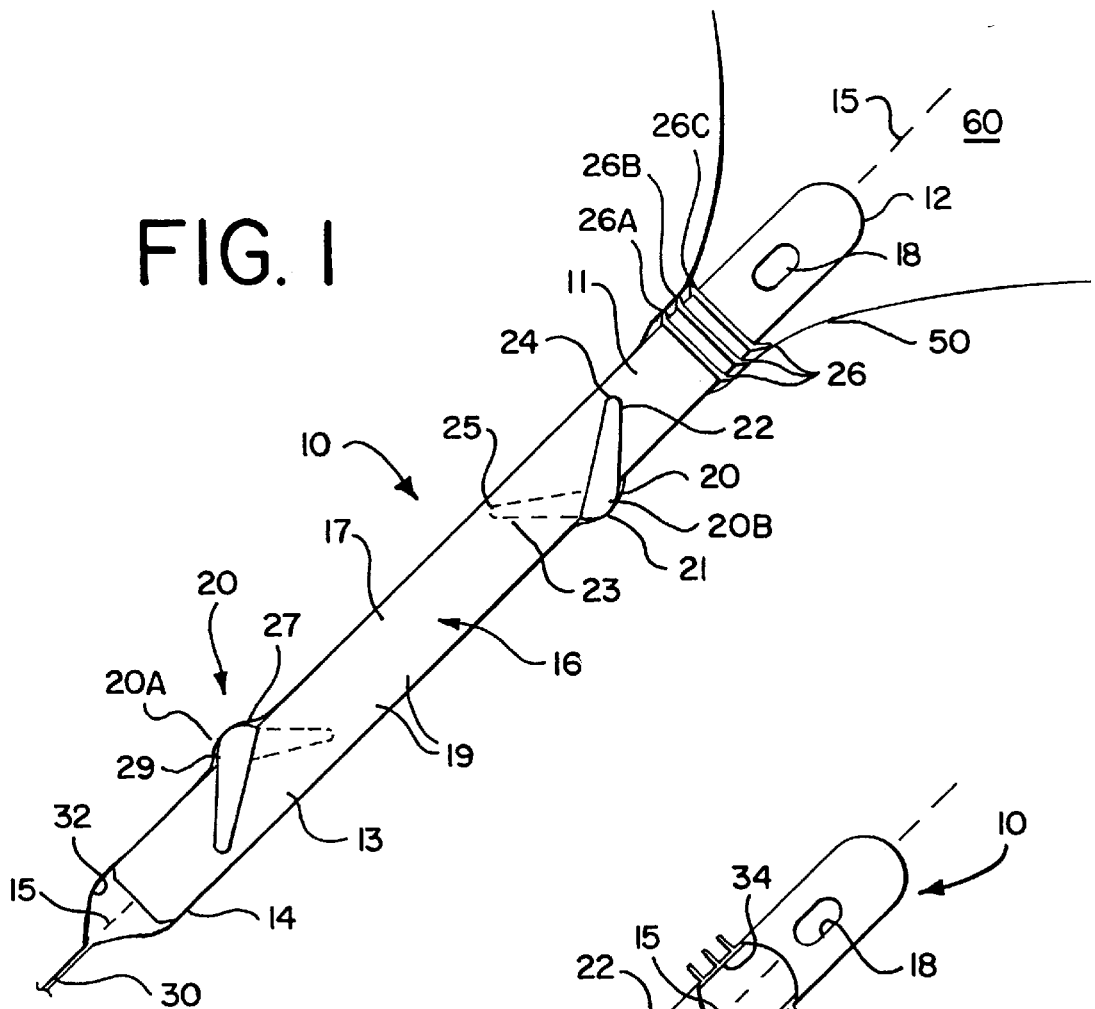
FIG. 1 is an expanded elevational view of one present embodiment showing an indwelling urethral device positioned within the urethra.
FIG. 2 is a partial sectional elevational view of the urethral device of the embodiment of FIG. 1.

First Embodiment: FIGS. 1 and 2 show a first preferred embodiment of a device 10. The device 10 is positioned in a urethra 30 and extends partially into a bladder 60 of a patient. The patient may be either a male or female human, or alternatively, embodiments of device may be used in other mammals or even other animals, with suitable changes in dimensions. The device 10 has a body 16 having a proximal portion 11 terminating in a proximal end 12 and distal portion 13 terminating in a distal end 14. The body 16 has a generally tubular shape around axis 15. The cross sectional shape of the body may be generally round or may be flattened to conform to the anatomical shape of the urethra. The body 16 includes a wall 17 having an exterior surface 19. The proximal portion 11 of the body 16 has at least one port 18 which may be located at the proximal end 12 to allow for urine flow into and through the device. Alternately, the proximal end 12 could have an open through-lumen to allow for the device to be used as an introducer for fluids, stents, or other devices or to function as a temporary stent itself for diagnostic and therapeutic procedures in the lower or upper urinary tract. The distal portion 13 of the device 10 can extend outside the body, or it can be retained entirely within the body. Those embodiments that extend outside the body can, for example, be connected to a fluid collection or introducer system, and embodiments retained entirely within the body can have additional elements or capabilities, such as a fluid valving or drug delivery.

Located along the length of the body 16 and extending outward from it are a plurality of anchors 20, such as anchors 20A and 20B, that aid in the insertion, withdrawal, and securing of the device within the urinary tract. In the embodiment of FIGS. 1 and 2, each of these anchors takes the form of a partial helical protrusion or ridge. These anchors 20 can vary in height, length, number, compressiveness, axial placement, material characteristics, and helix angle from 0 to 300 degrees, and more preferably from 15 to 300 degrees. Each anchor includes a leading edge 22 and a trailing edge 23 which taper from a middle portion 21 of the anchor for atraumatic insertion and withdrawal of the device. The anchors 20 can have the same or different amplitudes along the body 16, so long as proper retention is achieved. The height or amplitude of each of the anchors 20 can vary between the points of divergence 24 and convergence 25 with the body 16 of the device and has a maximum amplitude occurring along the middle portion 21. The maximum amplitude may extend along the entire length of the middle portion 21 of the anchor, or may extend along only part of the middle portion. Further, the maximum amplitude may be located approximately midway between the points 24 and 25 or may be located toward either the leading or trailing edges. The maximum amplitude of each anchor may be up to 100% of the base diameter of body 16 in extreme cases where the urethra is relatively atonic. The height of each anchor 20 defines a proximal surface 27 and distal surface 29. In the present embodiment, the profile of each anchor along its length is in a shape comparable to a half sinusoid. In a present embodiment, the anchors 20 are composed of the same material as the body 16 and are formed as part of a molding process during which the body is also formed. Alternatively, the anchors may be attached to the body after formation by suitable means, such as fusing, adhesives, etc.

Each anchor has a length that extends in a direction around the surface of the tubular body 16. In a present embodiment, each anchor extends only part way, i.e. less than 360°, around the circumference of the tubular body 16, and more preferably each anchor has a length such that it extends less than 180° around the circumference of the body. In some embodiments, each anchor may extend less than 90° around the circumference of the body. In an alternative embodiment, the middle portion 21 of the anchor extends only part way, i.e. less than 360° or more preferably less than 180°, around the circumference of the tubular body 16; however, the leading and trailing edges 22 and 23 associated with the anchor may extend the overall length of the anchor with the edges such that the points of convergence and divergence 25 and 24 may be greater than 360° apart from each other.

To minimize trauma to the urethra 30, the anchors 20 are preferably few in number (2–16, and more preferably 2–6) and are located in a random or non-uniform pattern along the length of body 16 as shown in FIGS. 1 and 2 so that the anchors 20 have a non-repeated pathway or point of contact with the urethral wall 32 as device 10 progresses along the urethra 30. Optionally, the anchors can have repeated pathways. In one embodiment, the plurality of anchors form a non-continuous helical ridge composed of individual helical sections each of which is less than a complete turn around the tubular body. The anchors 20 and their locations overcome a deficiency in the prior art that relies upon a complete or continuous helical surface to advance and seal a device in the urethra. A complete or continuous helical surface provides a perpetual, or time-prolonged, shunt pathway for urine. By not providing a continuous pathway, as shown in FIG. 1, the urethral wall is allowed to seal against the flat surfaces of the body thereby providing improved retention.

In the one preferred embodiment, the device 10 does not extend outside the body but resides entirely within the urinary tract, preferably primarily within the urethra, except to the extent to which the proximal end 12 extends partially or completely into either the bladder 60 or the bladder neck 50. Although the device 10 may be as long or longer than the urethra, in one preferred embodiment it is preferably less than 10 cm in versions for male users and 5 cm in versions for female users. There are, however, certain applications, including certain short-term applications, that would benefit from having an alternate embodiment of the device (not shown) wherein the device has a length such that a distal end 14 extends outside the body while still having the proximal end 12 positioned within the bladder or the bladder neck. The device 10 has a preferred size from approximately 10 French to 34 French to accommodate the range of urethral sizes from infants to adults, although sizes larger and smaller may be used if suitable, including sizes as small as 6 French. In one presently preferred embodiment, the outside surface of the device 10 is constructed of either molded silicone or latex. Alternative materials include molded polyurethane, polyethylene, polycarbonate, or other biocompatible materials.

Along the proximal portion 11 of the device 10 are one or more sealer rings 26, such as sealer rings 26A, 26B, and 26C. These sealer rings 26 assist in preventing the flow of urine around the outside of the device. These sealer rings are optional. These sealer rings 26 extend around the full circumference of the tubular body 16 and can vary in height, length, number, compressiveness, axial placement, material characteristics, and helix angle. Because the proximal-most sealer ring or rings may be located in the bladder neck 50 or bladder 60, which has a larger diameter than the urethra 30, these proximal-most sealer rings 26 may have a greater height than any sealer rings which are located more distally. The sealer rings 26 and the pressure of the urethra 30 against the flat surfaces (i.e., portions without anchors) of the tubular body 16 of the device 10 prevent the leakage of urine around the outside of the tubular body 16. Although the sealer rings 26 may be located only at the proximal portion 11 to prevent urine leakage to escape distally, additional sealer rings 26 may also be located at the distal portion 13 or elsewhere along the length of the tubular body 16. Optionally, the function of the sealer rings 26 can be replaced with surface coatings, by selecting the size of the tubular body 16 to have more intimate contact with the urethra 30, or by changing the material composition or characteristics of the device 10.

A preferred characteristic of the sealer rings 26 is pliability. As the device 10 is advanced through the urethra 30, such as during placement, the sealer rings 26 are oriented downwardly (i.e., distally). After the device 10 is fully inserted, a slight reverse movement of the device causes the sealer rings 26 to flip to an upward position (proximally). In this position, the downward pressure of urine against the sealer rings 26 causes them to depress downward (but not flip downward) and seal tightly against the urethra 30, thus preventing leakage of urine around the exterior of the device 10. In one embodiment the device 10 is produced using a composite construction of a base tube and cast external features. A base tube is constructed as a braid reinforced silicone tube using a stainless steel wire braid and Shore A 60 durometer silicone compound as the tube polymer (tubing produced by New England Electric Wire Corp. Lisbon, N.H.). The internal diameter of the base tube is 0.160 inches using a braid core diameter of 0.180 inches. The external diameter of the base tube is 0.210 inches. Anchor features are then cast onto the outer circumference using a Shore A 30 Durometer silicone rubber compound. The specific compounds used for casting the anchoring and sealing features are RTV 430 silicone rubber resin and Beta 11-D1 silicone catalyst solution, both manufactured by GE Silicones of Waterford, N.Y. Alternate embodiments of the device can be made by allowing the external features' hardness to vary using compounds with Shore A Durometers ranging from 10 to 80.

Referring to FIG. 2, there is shown a partial, sectional view of the device 10. The body 16 defines a passageway or lumen 31 that extends through the length of the body 16 from the proximal port 18 to a distal opening 33. A marker 34 (which may be metallic or other suitable material) is located near the proximal end 12 of device 10 and functions to help locate or position the device using ultrasound, x-ray, or other technology. The first partial view of the distal end 14 shows an inner recess 42 in the lumen 31 immediately proximal of the distal opening 33. The inner recess 42 is shaped to receive a proximal end of an insertion tool 100 (shown in FIG. 3 and described in detail in copending application Ser. No. 60/036,944, filed Feb. 7, 1997, the entire disclosure of which is incorporated herein by reference). The second partial view further shows a braid 44 which is embedded in or located inside the tubular body 16 and which provides for radial size stability and torsional stability while the device 10 is being inserted and removed. A preferred material for the braid is 316L Hard Stainless Steel wire of 0.002 inch diameter (wire gage 44). The braid's preferred construction is 2 ends per carrier with 16 carriers. The braid's preferred pitch is approximately 14 picks per inch. This braid construction generates a braid angle of 45.3 degrees for adequate torsional stiffness and 15.1% coverage which allow adequate bond areas for subsequent polymer attachment. Alternately, the braid 44 may be a round wire in sizes from 0.001 to 0.010 inch in diameter or larger, or flat wire ranging in sizes from 0.0005×0.0025 to 0.006×0.015.

Placement of the Urethral Device: Referring to FIGS. 3 through 5, the insertion tool 100 can be used to couple with the device 10 to aid insertion, or the insertion tool 100 and device 10 may each optionally be provided with various electrical, optical, fluid, or mechanical circuits, channels, or linkages that cooperate together to provide feedback signals that indicate the location of the device and/or that the device is properly located with respect to anatomical features.

The insertion tool 100 has a handle 102 and a linkage 104 that passes through a shaft 106 thereof. The linkage 104 is connected to an actuating mechanism in the handle 102, such as a plunger 108. Actuating the plunger 108 changes the shape and/or diameter of a deformable coupling 110 located at a proximal end of the insertion tool so that the deformable coupling 10 has a smaller first profile prior to coupling with the distal end 14 of device 10 (FIG. 4) and a second larger profile when coupled to device 10 (FIG. 5).

To use the insertion tool to position the device 10, the insertion tool 100 and the device are coupled together as shown in FIG. 3. The device is inserted into the urethra. The device may be inserted with a combined rotational and forward (proximal) movement, or alternatively, the device may be inserted with forward movement only. Upon appropriate positioning of the device, which can be facilitated by suitable indicating means, such as ultrasound, x-ray, or any of the indicating means disclosed in the copending application Ser. No. 60/036,944, the insertion tool is decoupled from the device and removed. The device is now positioned for short- or long-term use.

As known in the art, anchoring of the device can be enhanced by the use of adhesives or adhesive-like compounds along all or a portion of the device. In addition, the exterior portion of the embodiment of the device that extends outside the body can further have a meatal flange or flared portion to prevent unwanted migration into the bladder, to contribute to anchoring the device, to further seal against leakage, and to absorb unwanted urine leakage. The meatal flange can be shaped to cooperate with the user's anatomy.

First Alternate Embodiment. FIGS. 6a through 8 illustrate an alternate embodiment 200 of the urethral device. In this embodiment, a urethral device is provided with foldable or highly bendable anchors 220 that allow for a dynamic response to the increased pressure placed on the device by either the urethra, bladder neck, bladder, or the fluids in the urethra or bladder. Each of the anchors 220 has an angulated recess 221 that is flexible in response to either urethral stresses or dynamic forces working on the device. The foldable characteristic still allows for rotational movement of the device within the urethra, while simultaneously allowing for a relatively non-traumatic anchoring when positioned.

Referring to FIGS. 6a through 8, some of the components are the same or similar to the components in the previously described embodiment and like components are labeled with the same numbers. In this embodiment, the anchors 220 are thinner, more flexible, and more responsive to pressure impulses incumbent upon the device 200. In a preferred embodiment, these anchors 220A and 220B are formed of partial helical ridges or protrusions. Because of their shape, angle, material characteristics, and dynamic nature, the anchors 220 may engage the urethral wall 32 somewhat more definitively than in the previous embodiment. FIG. 6a illustrates the device 200 in a relatively unstrained position, and FIG. 6b illustrates the device 200 in a relatively more engaged position. To be most effective, a distal surface 241 of each of these anchors 220 forms an acute angle (shown at 246) of approximately 30degrees or greater, and preferably approximately 45 degrees, with the exterior surface 19 of the tubular body 16 as shown in FIG. 7. The proximal surface 243 of each of these anchors 220 may form an obtuse angle with the exterior surface 19 of the tubular body 16. When the device 200 undergoes pressure from urine accumulation in the bladder or experiences pressure impulses from coughing, laughing, exercising, or other such stresses, the device 200 may have a slight tendency to be displaced distally. Overcoming these forces will be the action of the anchors 220 against the urethral wall 32. When pressure or impulses are placed upon the device 200 and when the device 200 experiences a slight distal displacement, the anchors 220 deflect radially and exert additional pressure against the urethral wall 32. In this manner, the anchors 220 serve not only to secure the device in place, but also to dampen pressure impulses incumbent upon it. Because the profile of the anchors 220 is foldable or highly flexible, the device 200 may be installed either with rotational motion or by moving from a distal position to a proximal position by a non-rotating, longitudinal motion only. Although the device 200 may be installed without rotation, non-traumatic removal may require rotational motion. FIG. 8 shows a partial sectional elevational view of the device 200, showing a distal inner recess 242 that is shaped to receive the proximal end of the insertion tool 100. Also shown using hidden lines is the length and position of the anchors 220. The height, length, number, axial placement, and helix angle of the anchors 220 may be similar to those described above in connection with the previous embodiment.

Figure 13:
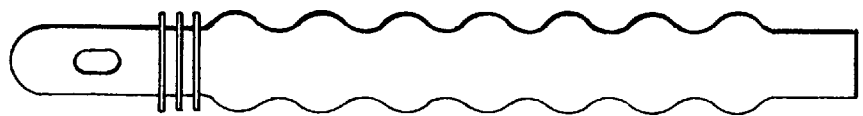
FIGS. 9–13 are elevational views of further alternate embodiments of the urethral device for human males.
Figure 12:
Figure 11:
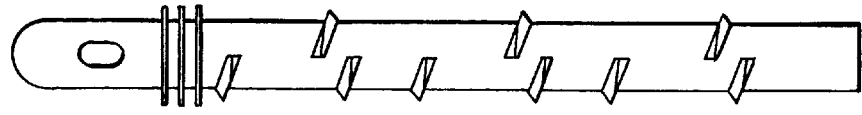
Figure 10:
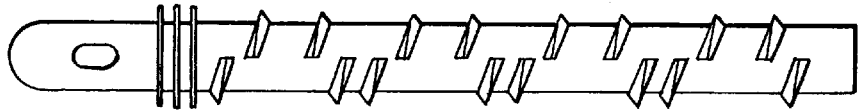
Figure 9:
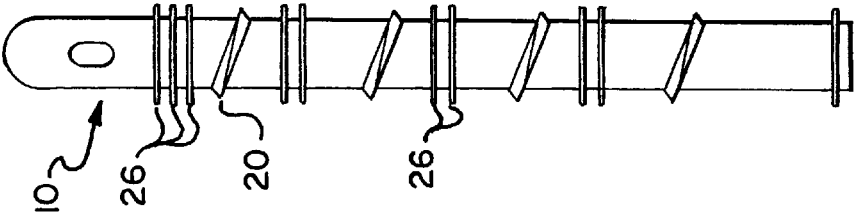

Additional Alternate Embodiments: In alternative embodiments, the optional sealer rings 26 may be located only at the proximal portion 11 or alternatively the sealer rings may be additionally located at the distal portion 13 of the device 10 (or the device 200). It is envisioned that the sealer rings 26 and anchors 20 (or 220) can be intermixed in any of a number of sequences, as shown in FIG. 9 through FIG. 13 which illustrate male versions of the device, and in FIG. 14 through FIG. 16 which illustrate female versions of the device. FIG. 9 shows an embodiment in which the sealer rings 26 and the anchors alternate along the length of the body. FIG. 10 shows an embodiment in which the sealer rings are located only at the proximal portion of the tubular body and wherein a relatively greater number of anchors are located along the length of the body in an irregular pattern. FIG. 11 shows an embodiment with relatively fewer anchors compared to the embodiment of FIG. 10 and in which the sealer rings are located only at the proximal portion. FIG. 12 shows an embodiment in which the anchors are formed of relatively wide undulations which spiral around the exterior surface of the tubular body and further which includes sealer rings located only at the proximal portion. FIG. 13 shows an embodiment in which the anchors are formed of relatively wide undulations which encircle (but do not necessarily spiral around) the exterior surface of the tubular body and further which includes sealer rings located only at the proximal portion. FIG. 14 shows a female version with proximal sealing rings and relatively few anchors which are formed of partial helical ridges. FIG. 15 shows a female version of the device in which sealer rings are located only at the proximal and distal portions and wherein the anchors are located along the middle portion of the body in an irregular pattern. FIG. 16 shows a female version of the device with sealer rings and anchors alternating along the length of the body. With respect to each of these various embodiments, portions of the exterior surface of the body that are free from both sealer rings and anchors can be used for the placement of elements that facilitate therapeutic or diagnostic procedures, such as ultrasound diagnosis, radio-frequency ablation, and drug delivery. The anchors or sealer rings can also be positioned to accommodate any of the various position sensing components described in the copending application Ser. No. 60/036,944.

FIGS. 17–18 show another embodiment 300 of the urethral device. In this embodiment, the anchors 320 are formed as offset sinusoidal protrusions along the body 16. These anchors 320 have relatively larger surface profiles that allow for more contact with the urethra 30 and that extend over a small portion of the exterior (FIG. 17) or over all of the exterior (FIG. 18).

Referring to FIGS. 24 and 24A, there is depicted another embodiment 500 of the urethral device. This device 500 is similar to the previously described devices and includes a tubular body 16. In this device the anchors 520 do not spiral around the tubular body 16 but instead encircle it, i.e., the point of divergence 524 is at the same axial position along the length of the tubular body 16 as the point of convergence 525. As in the other embodiments, each anchor 520 has a middle portion 521 having a greater height or amplitude, and leading and trailing end portions, 522 and 523, that taper from the middle portion 521 to the points of divergence and convergence 524 and 525. As described above, the maximum amplitude may extend along the middle 8 portion 521 or may be located toward one of the end portions.

Referring to FIGS. 25 and 25A, there is depicted another embodiment 600 of the urethral device. This device 600 is similar to the device depicted in FIGS. 24 and 24A, except that the device 600 has six anchors 620 instead of only two. As in the previously described embodiments, the anchors 620 are preferably located in a random or irregular pattern.

Referring to FIGS. 26 and 26A, there is depicted another embodiment 700 of the urethral device. This device 700 is similar to the devices depicted in FIGS. 24, 24A, 25 and 25A except that the device 700 has rectangular anchors 720 that extend generally longitudinally along the length of the body. These anchors 720 are parallel to the axis 15 of the tubular body 16 and serve to keep the device 10 positioned in place. These anchors 720 are preferably located in a random or irregular pattern.

Valved Embodiments: According to a further aspect, the device may include a valving mechanism to control the flow of fluid through the device. Any of the above described embodiments of devices for positioning in the urethra are compatible with the implementation of valves or other urine-control elements. Valved embodiments may require more or larger anchors than unvalved devices because of the additional forces incumbent upon the valve. Thus, surface and size modifications of the device can be purposefully made to produce an adequately anchored device.

FIG. 19 through FIG. 23 illustrate one such embodiment 400 of a valved urethral device. The tubular body portion 416 of the valved device 400 may be similar to any of the above described embodiments. The device 400 has a proximal end 412, a body 416, and a port 418. (The distal portion of the device 400 is not shown.) Within the body 416 is a magnetic assembly comprising a magnetic tumbler 480 (shown in elevational views in FIG. 20) that is held in place axially by a pin 482 and a journal 483 which cooperates with a shaft 484 of a stopper 486. The pin 482 is supported by a distal support flange 485 (shown in more detail in FIG. 21), and the shaft 484 is supported by the proximal support flange 487 (shown in more detail in FIG. 22).

The distal end 488 of the shaft 484 is cam-lobe shaped and fits in a latch insert 490 of the magnetic tumbler 480. In the closed position, the distal end 488 of the shaft 484 is in a non-aligning orientation with a keyway 492. When the magnetic tumbler 480 is caused to rotate by use of a magnet 470 located external of the body, the distal end 488 of the shaft 484 aligns with and moves distally along the keyway 492 of a latch insert 490, causing the stopper 486 to likewise move distally and open a fluid-flow channel 494 of a seat 496. The flow of fluid (in this case, urine) causes the stopper 486 to remain in a distal or open position.

This rotation and resulting alignment and cooperation of parts results in a magnetic latching system that is an improvement over prior systems. The magnetic torque required to rotate the magnetic tumbler 480 and thus activate the flow of fluid is much less in the disclosed system compared to a prior art system that requires magnetic torque to overcome a magnetic circuit between two parts. In the disclosed system, the magnetic tumbler 480 is not required to overcome a direct hydraulic force without mechanical advantage but rather is required to overcome only minimal frictional forces to "unlatch" the stopper 486. After the disclosed system is unlatched, the hydraulic pressure within the fluid provides the necessary work and force necessary to displace the proximal end 497 of the stopper 486 from the seat 496 and open the fluid-flow channel 494. Activation of this latching system requires a minimum force of magnetic field.

The magnetic tumbler 480 in the disclosed embodiment is preferably made of Neodynium or Symarium-Cobolt. The magnetic flux density of the magnetic tumbler 480 is preferably greater than 7500 Gauss. The external magnet 470 of the disclosed embodiment is constructed of the same material but has a greater physical dimension. The external magnet 470 is preferably cylindrical and poled axially with a diameter of 0.75 inches and a length of 3 inches. The latch insert 490 is preferably made of a low nonmagnetic material which has a low coefficient of friction such as PTFE.

When fluid flow has nearly or completely ceased, the combined force of springs 498a, 498b and 498c, which act upon the proximal end 497 of the stopper 486, has sufficient magnitude to displace the distal end 488 of the stopper 486 within the keyway 492 and then lightly compress the proximal end 497 of the stopper 486 against the seat 496, thus closing the fluid-flow channel 494. The springs 498a, 498b, and 498c are constructed of 304 high-tensile stainless steel and provide a maximum combined force of less than 0.3 grams when the stopper 486 is in the open position. The force of the springs 498a, 498b, and 498c is insufficient to overcome the hydraulic pressures that are incumbent upon the proximal end 497 of the stopper 486. The resultant axial displacement versus force profile is nonlinear.

When fluid flow ceases, the stopper 486 is returned proximally to a closed position by the springs 496a, b and c, which position the stopper 486 in a closed position. The proximal end 497 of the stopper 486 is slightly deformable to make a better seal with the seat 496. The proximal end 497 of the stopper 486 is preferably made of a low-durometer material with a durometer less than 100 Shore A.

The magnetic tumbler 480 then rotates back to its initial position prior to initiation. The re-indexing occurs due to the light magnetic field coupled between the tumbler 480 and the metal index surface 493 on the body 416.

The magnetic tumbler 480, the seat 496, the proximal support flange 487, and the distal support flange 485 are all shaped with through-holes or passages to allow for the maximum fluid flow volume. Urine flows in through the port 418, through the magnet assembly, through the inner lumen 499, and out the distal end of the device 400.

As a safety feature, the proximal end 497 of the stopper 486 deflects in the event that pressurization of the fluid exceeds approximately 40 cm of water for a time period of several seconds without intermittence. This feature allows for the relieving of a bladder that is excessively pressurized in order to prevent reflux into the kidneys.

Advantages of the Disclosed Embodiments: The disclosed embodiments provide several advantages over prior devices intended for urethral placement. The disclosed embodiments provide for some or all of the following advantages relative to prior devices: (1) ease of insertion, (2) secure retention in the urethra, (3) a mechanical advantage that permits a device with a larger effective diameter to be inserted in the urethra with the effect of inserting a smaller device, (4) minimal trauma and irritation to the urethra, and (5) improved sealing of the device with the urethra to prevent leakage of urine around the perimeter of the device.

1. Ease of Insertion. Insertion and removal of some of the disclosed devices may be facilitated by the rotational movement of the device. The rotation provides for the advancement or retraction due to the interaction of the relatively short anchors, in particular in the embodiments in which the anchors have helical surfaces, with the surface of the urethra with which they are in contact. Additionally, each surface is provided with a varying height which is similar to an elongated sinusoidal profile to further reduce abrasion during the positioning of the device.

2. Secure Retention. Once in place, the urethra or bladder neck is better able to conform to the anchors and provide for secure retention. Minimizing the length and surface area of the individual anchors with the urethra allows for reduction of stress. Increasing the area of the flat, extended surfaces between the anchors and keeping to a minimum the area of the protrusions themselves aids in securing the device because the urethra will provide some friction with the flattened surface as well. An effective balance between the flat (non-anchors) and raised (anchors) areas of the device can be achieved to provide for secure retention while minimizing the areas of the urethra that are stressed due to contact with the anchors. Using the minimum number of anchors necessary to effectively secure the device allows a large portion of the urethra to be in a more relaxed, natural state. This is particularly important due to the vulnerability of the urinary tract to infections. Damage to the inner mucosal layer may be a major contributor to an individual's susceptibility to urinary tract infections. Some or all of the disclosed embodiments minimize the surface irritation during positioning and retention and further minimize the effect of restriction of intercapillary blood circulation which effectively perfuses the urethra and the surrounding tissues by limiting the continuous length of the stressed urethral surface.

3. Mechanical Advantage. Some or all of the disclosed embodiments permit a device with a larger effective diameter to be inserted in the urethra with the effect of inserting a smaller device. As the anchors engage the urethral wall while the device is being inserted, the device is advanced through the urethra.

4. Minimum of Trauma and Irritation. The anchors may be patterned in a non-uniform manner in order to minimize any abrasion of the intraurethral mucosa due to repeated contact of anchors with the urethra as the device is moved along the passageway. A uniform pattern might cause the same areas of the urethra to be contacted by succeeding anchors as the device is rotated.

5. Sealing. As described above, in the preferred embodiments the anchors are not used for sealing. Instead, sealing is accomplished by one or both of the following. The first means by which sealing is achieved is by the wall of the urethra bearing against and sealing against the relatively long, flat surfaces between the anchors of the device. The second means by which sealing is achieved is by the use of a secondary system of soft and pliable circumferential sealer rings designed specifically for restriction of fluid flow along the exterior of the device. These sealing rings are not designed to secure the device, but rather to restrict the flow in a non-traumatic manner.

It is to be understood, however, the even though numerous characteristics and advantages of the present invention have been set forth in the foregoing description, together with details of the structure and function of present invention, the sequence or order of the specific steps, or the actual compositions, environmental conditions, and the like experienced or sensed may vary somewhat. Furthermore, it will be appreciated that this disclosure is illustrative only and that changes may be made in detail, especially in matters of shape, size, arrangement of parts, or sequence of elements of the various aspects of the invention within the principles of the invention to the full extent indicated by the broad general meaning of the terms in which the appended claims are expressed.

I claim:

1. A device for placement in a urethra comprising:
   a tubular body sized for placement in said urethra, said tubular body having a proximal portion adapted for placement toward a bladder end of said urethra and a distal portion opposite from said proximal portion, said tubular body having an exterior surface; and
   a plurality of anchors extending outward from said exterior surface, wherein each of said plurality of anchors extends less than 360° around said exterior surface.

2. The invention of claim 1 wherein each of said plurality of anchors extends less than 180° around said exterior surface.

3. The invention of claim 1 wherein each of said plurality of anchors extends less than 90° around said exterior surface.

4. The invention of claim 1 wherein each of said plurality of anchors has associated therewith tapered end portions extending from a main portion thereof and tapering toward said exterior surface of said tubular body.

5. The invention of claim 1 wherein each of said plurality of anchors is comprised of an elongate ridge having a height extending in a radial direction relative to an axis of said tubular body, and a length extending in a direction generally around a circumference of said tubular body, and wherein said height varies along said length tapering from a maximum height located along said length of said ridge.

6. The invention of claim 1 wherein each of said plurality of anchors extends helically around said exterior surface.

7. The invention of claim 1 wherein said tubular body comprises a wall that defines a passageway extending from said proximal portion to said distal portion and further wherein said tubular body has a proximal opening located in said proximal portion and communicating with said passageway and a distal opening located in said distal portion and communicating with said passageway.

8. The invention of claim 7 wherein a distal portion of said passageway includes a recess for receiving an insertion tool.

9. The invention of claim 7 wherein the proximal opening comprises an open through-lumen.

10. The invention of claim 7 wherein the proximal opening comprises a port.

11. The invention of claim 7 further comprising a valve located in said passageway.

12. The invention of claim 1 wherein said tubular body has a length such that said distal portion extends outside the urethra during use.

13. The invention of claim 1 wherein said tubular body has a length such that a distal end is retained inside the urethra during use.

14. The invention of claim 1 wherein said tubular body has a length such that a proximal end is positioned in the bladder during use.

15. The invention of claim 1 wherein at least one of said plurality of anchors has a height different from a height of another of said plurality of anchors.

16. The invention of claim 1 wherein each of said plurality of anchors has a maximum height of approximately 100% of a base diameter of said tubular body.

17. The invention of claim 1 wherein said plurality of anchors are located in a non-uniform pattern along a length of said tubular body.

18. The invention of claim 1 wherein said plurality of anchors define non-repeated pathways along a length of said tubular body.

19. The invention of claim 1 wherein said device has a size between 6 and 24 French.

20. The invention of claim 1 wherein said exterior surface is constructed of a material selected from a group consisting of: molded silicone, latex, polyurethane, polyethylene, and polycarbonate.

21. The invention of claim 1 further comprising:
   at least one sealer ring located on said proximal portion and extending around said tubular body.

22. The invention of claim 21 wherein said at least one sealer ring is formed of a pliable material.

23. The invention of claim 1 further comprising:
   at least one sealer ring located on said distal portion and extending around said body.

24. The invention of claim 1 further comprising:
   a plurality of sealer rings located on said proximal portion and extending around said body.

25. The invention of claim I wherein said body is formed of silicone rubber.

26. The invention of claim 1 wherein said body is formed of a material having a Durometer hardness in a range between approximately 20 and 80 Shore.

27. The invention of claim 1 wherein said body is formed of a material having a Durometer hardness of approximately 60 Shore.

28. The invention of claim 1 further comprising a marker located at said proximal portion.

29. The invention of claim 1 wherein said tubular body comprises a wall that defines a passageway extending from said proximal portion to said distal portion and further wherein said tubular body has a proximal opening located in said proximal portion and communicating with said passageway and a distal opening located in said distal portion and communicating with said passageway, and further wherein a magnetically-actuatable valve is located in said passageway.

30. The invention of claim 1 wherein said plurality of anchors are located in a uniform pattern along a length of said tubular body.

31. The invention of claim 1 wherein said plurality of anchors define repeated pathways along a length of said tubular body.

32. A device for placement in a urethra comprising:
  a tubular body sized for placement in said urethra, said tubular body having a cylindrical-shaped wall having an exterior surface, said tubular body having a proximal portion adapted for placement toward a bladder end of said urethra and a distal portion opposite from said proximal portion; and
  a plurality of anchors located on said exterior surface, each of which is comprised of an elongate ridge having a height extending in a radial direction relative to an axis of said tubular body, a length extending in a direction generally around a circumference of said tubular body, and a width perpendicular to said length and parallel to said axis, and wherein said ridge has a middle portion along its length where its height defines a distally-oriented surface that engages a wall of said urethra to anchor said tubular body therein, wherein said middle portion extends less than 360° around said exterior surface of said tubular body.

33. The invention of claim 32 wherein said tubular body defines a passageway extending from said proximal portion to said distal portion, said tubular body having a proximal opening located in said proximal portion and communicating with said passageway and a distal opening located in said distal portion and communicating with said passageway.

34. A tubular device for placement in a urethra to provide a passageway therein comprising:
  a tubular body sized for placement in the urethra, said tubular body having a cylindrical-shaped wall having an exterior surface, said tubular body defining a lumen extending from a proximal portion to a distal portion thereby providing a passageway through said tubular body, said proximal portion adapted for placement toward a bladder end of the urethra; said tubular body having a proximal opening located in said proximal portion and communicating with said lumen and a distal opening located in said distal portion and communicating with said lumen;
  a plurality of anchoring ridges, wherein each of said plurality of anchoring ridges extends from said exterior surface and has a distally-facing surface, and wherein each of said plurality of anchoring ridges extends less than 360° around said exterior surface.

35. The invention of claim 34 wherein said distally-facing surface forms an acute angle with said exterior surface of said tubular body.

36. The invention of claim 34 wherein said distally-facing surface forms an angle of at least approximately 30° with said exterior surface of said tubular body.

37. The invention of claim 34 wherein said anchoring ridges deflect radially when pressure is applied to said tubular body.

38. The invention of claim 34 wherein each of said plurality of anchoring ridges has a proximally-facing surface, and wherein said proximally-facing surface forms an obtuse angle with said exterior surface of said tubular body.

39. The invention of claim 34 wherein each of said plurality of anchoring ridges is longitudinally displaced from one another along said exterior surface.

40. A device for placement in a urethra to provide a passageway therein comprising:
  an elongate tubular body sized for placement in the urethra, said tubular body having a cylindrical-shaped wall having an exterior surface, said tubular body defining a lumen extending from a proximal portion to a distal portion thereby providing said passageway, said proximal portion adapted for placement toward a bladder end of said urethra; said tubular body having a proximal opening located in said proximal portion and communicating with said lumen and a distal opening location in said distal portion and communicating with said lumen;
  a first anchor extending outward from said exterior surface and extending around said exterior surface through an angle of less than 360°; and
  at least one additional anchor extending outward from said exterior surface and extending around said exterior surface through an angle of less than 360°, said at least one additional anchor longitudinally displaced from said first anchor.

41. The invention of claim 40 wherein said at least one additional anchor is displaced circumferentially from said first anchor.

42. The invention of claim 40 wherein said first anchor and said at least one additional anchor each extend less than 180° around said exterior surface.

43. The invention of claim 40 wherein each of said anchors extends less than 90° around said exterior surface.

44. The invention of claim 40 wherein each of said anchors extends helically around said exterior surface.

45. The invention of claim 40 further comprising:
  a tapered leading edge associated with each of said anchors and extending from its associated anchor to a point of divergence with said exterior surface; and
  a tapered trailing edge associated with each of said anchors and extending from its associated anchor to a point of convergence with said exterior surface.

46. A device for placement in a urethra comprising:
  a tubular body defining an interior passageway and having proximal and distal opening communicating therewith, wherein a proximal end of said tubular body is oriented toward the bladder when positioned in the urethra; and
  a non-continuous spiral ridge located on an exterior surface of said tubular body and extending outwardly therefrom, said non-continuous spiral ridge comprised of a plurality of continuous spiral sections wherein each of said continuous spiral sections extends less than 360° around said tubular body.

47. A device for placement in a urethra comprising:
  a tubular body sized for placement in said urethra, said tubular body having a proximal portion adapted for placement toward a bladder end of said urethra and a distal portion opposite from said proximal portion, said tubular body having an exterior surface; and
  a plurality of anchors extending outward from said exterior surface wherein said anchors form a sinusoidal protrusion along a side of the exterior surface.

48. A device according to claim 47 wherein said anchors extend 360° around said exterior body.

49. A device according to claim 47 wherein said anchors extend less than 360° around said exterior body.

50. A device according to claim 47 wherein the sinusoidal protrusion along the side of the exterior surface is offset from a sinusoidal protrusion along a second side of the exterior surface.

51. A device according to claim 47 wherein the sinusoidal protrusion along the side of the exterior surface is aligned with a sinusoidal protrusion along a second side of the exterior surface.

52. The invention of claim 47 wherein each of said plurality of anchors extends less than 180° around said exterior surface.

53. The invention of claim 47 wherein each of said plurality of anchors extends less than 90° around said exterior surface.

54. The invention of claim 47 wherein each of said plurality of anchors extends helically around said exterior surface.

55. The invention of claim 47 wherein said tubular body comprises a wall that defines a passageway extending from said proximal portion to said distal portion and further wherein said tubular body has a proximal opening located in said proximal includes a recess for receiving an insertion tool.

56. The invention of claim 55 wherein the proximal opening comprises an open through-lumen.

57. The invention of claim 55 wherein the proximal opening comprises a port.

58. The invention of claim 55 further comprising a valve located in said passageway.

59. The invention of claim 47 wherein said tubular body has a length such that said distal portion extends outside the urethra during use.

60. The invention of claim 47 wherein said tubular body has a length such that a distal end is retained inside the urethra during use.

61. The invention of claim 47 wherein said tubular body has a length such that a proximal end is positioned in the bladder during use.

62. The invention of claim 47 wherein said device has a size between 6 and 24 French.

63. The invention of claim 47 wherein said exterior surface is constructed of a material selected from a group consisting of: molded silicone, latex, polyurethane, polyethylene, and polycarbonate.

64. The invention of claim 47 further comprising:

at least one sealer ring located on said proximal portion and extending around said tubular body.

65. The invention of claim 64 wherein said at least one sealer ring is formed of a pliable material.

66. The invention of claim 47 further comprising:

at least one sealer ring located on said distal portion and extending around said body.

67. The invention of claim 47 further comprising:

a plurality of sealer rings located on said proximal portion and extending around said body.

68. The invention of claim 47 wherein said body is formed of silicone rubber.

69. The invention of claim 47 wherein said body is formed of a material having a Durometer hardness in a range between approximately 29 and 80 Shore.

70. The invention of claim 47 wherein said body is formed of a material having a Durometer hardness of approximately 60 Shore.

71. The invention of claim 47 further comprising a marker located at said proximal portion.

72. The invention of claim 47 wherein said tubular body comprises a wall that defines a passageway extending from said proximal portion to said distal portion and further wherein said tubular body has a proximal opening located in said proximal portion and communicating with said passageway and a distal opening located in said distal portion and communicating with said passageway, and further wherein a magnetically-actuatable valve is located in said passageway.

73. A device for placement in a urethra comprising:

a tubular body sized for placement in said urethra, said tubular body having a proximal portion adapted for placement toward a bladder end of said urethra and a distal portion opposite from said proximal portion, said tubular body having an exterior surface; and a plurality of anchors extending outward from said exterior surface wherein said anchors form an undulating pattern along said exterior surface.

74. A device according to claim 73 wherein said anchors extend 360° around said exterior body.

75. A device according to claim 73 wherein said anchors extend less than 360° around said exterior body.

76. A device according to claim 73 wherein the sinusoidal protrusion along the side of the exterior surface is offset from a sinusoidal protrusion along a second side of the exterior surface.

77. A device according to claim 73 wherein the sinusoidal protrusion along the side of the exterior surface is aligned with a sinusoidal protrusion along a second side of the exterior surface.

78. A device according to claim 73 wherein each of said plurality of anchors extends less than 180° around said exterior surface.

79. The invention of claim 73 wherein said tubular body comprises a wall that defines a passageway extending from said proximal portion to said distal portion and further wherein said tubular body has a proximal opening located in said proximal includes a recess for receiving an insertion tool.

80. The invention of claim 79 wherein the proximal opening comprises an open through-lumen.

81. The invention of claim 79 wherein the proximal opening comprises a port.

82. The invention of claim 79 further comprising a valve located in said passageway.

83. The invention of claim 73 wherein said tubular body has a length such that said distal portion extends outside the urethra during use.

84. The invention of claim 73 wherein said tubular body has a length such that a distal end is retained inside the urethra during use.

85. The invention of claim 73 wherein said tubular body has a length such that a proximal end is positioned in the bladder during use.

86. The invention of claim 73 wherein said device has a size between 6 and 24 French.

87. The invention of claim 73 wherein said exterior surface is constructed of a material selected from a group consisting of: molded silicone, latex, polyurethane, polyethylene, and polycarbonate.

88. The invention of claim 73 further comprising:

at least one sealer ring located on said proximal portion and extending around said tubular body.

89. The invention of claim 88 wherein said at least one sealer ring is formed of a pliable material.

90. The invention of claim 73 further comprising:

at least one sealer ring located on said distal portion and extending around said body.

91. The invention of claim 73 further comprising:

a plurality of sealer rings located on said proximal portion and extending around said body.

92. The invention of claim 73 wherein said body is formed of silicone rubber.

93. The invention of claim 73 wherein said body is formed of a material having a Durometer hardness in a range between approximately 29 and 80 Shore.

* * * * *

UNITED STATES PATENT AND TRADEMARK OFFICE
CERTIFICATE OF CORRECTION

PATENT NO. : 5,971,967
DATED : October 26, 1999
INVENTOR(S) : Lloyd K. Willard

It is certified that error appears in the above-identified patent and that said Letters Patent is hereby corrected as shown below:

Claim 25,
Line 1, delete "claim I" and substitute -- claim 1 --.

Claim 55,
Line 5, after "proximal" insert -- portion --.

Claim 79,
Line 5, after "proximal" insert -- portion --.

Signed and Sealed this

Twenty-eighth Day of August, 2001

Attest:

NICHOLAS P. GODICI
Attesting Officer
Acting Director of the United States Patent and Trademark Office